United States Patent [19]

Matsuhira

[11] Patent Number: 4,743,707
[45] Date of Patent: May 10, 1988

[54] PROCESS FOR PURIFYING ALLYL ALCOHOL

[75] Inventor: Shinya Matsuhira, Oita, Japan

[73] Assignee: Showa Denko Kabushiki Kaisha, Tokyo, Japan

[21] Appl. No.: 876,588

[22] Filed: Jun. 20, 1986

[51] Int. Cl.[4] .................. C07C 29/86; C07C 33/03; C07C 29/80
[52] U.S. Cl. .................................................. 568/919
[58] Field of Search .................................. 568/919

[56] References Cited

U.S. PATENT DOCUMENTS

| | | | |
|---|---|---|---|
| 2,595,763 | 5/1952 | Carlson et al. | 568/919 |
| 4,454,359 | 6/1984 | Colgrove et al. | 568/919 |
| 4,544,779 | 10/1985 | Bright | 568/919 |
| 4,594,466 | 6/1986 | Reeves | 568/919 |

FOREIGN PATENT DOCUMENTS 5647 of 1890 United Kingdom ................ 568/919

OTHER PUBLICATIONS

Lange, "Handbook of Chemistry," 10th ed., 1961, pp. 394 and 395.
The Merck Index, 6th ed., 1952, pp. 34 and 35.
Lange, "Handbook of Chemistry," 10th ed., 1961, pp. 290, 291, 306 and 307.

Primary Examiner—J. E. Evans

[57] ABSTRACT

A process for purifying allyl alcohol, comprising adding at least one member selected from the group consisting of dipotassium hydrogenphosphate, potassium phosphate, potassium pyrophosphate, potassium tripolyphosphate and potassium carbonate to an aqueous solution of allyl alcohol to separate the solution into an aqueous phase and an organic phase, removing the aqueous phase, and optionally subjecting the organic phase to distillation to obtain allyl alcohol having a high purity.

4 Claims, 1 Drawing Sheet

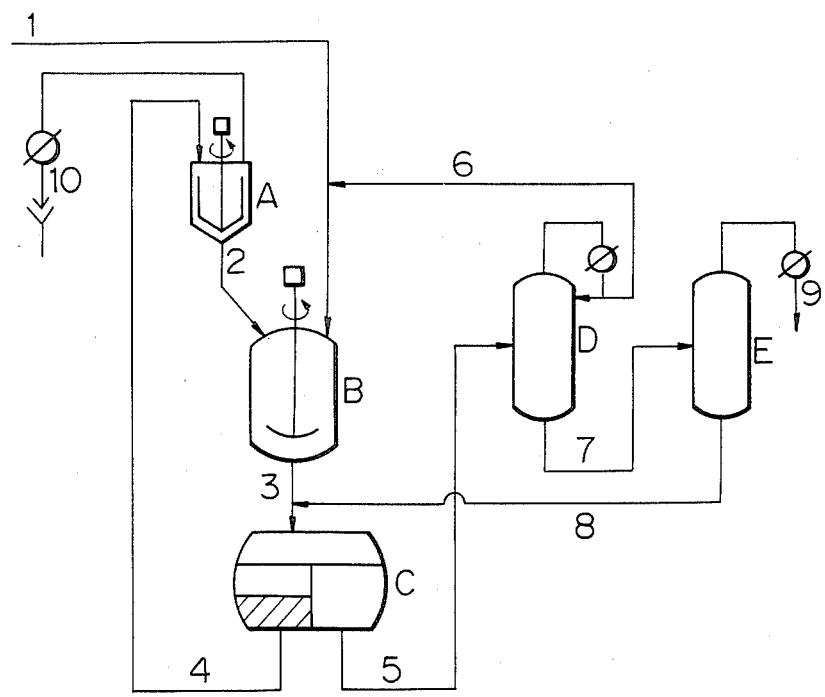

PROCESS FOR PURIFYING ALLYL ALCOHOL

BACKGROUND OF THE INVENTION

1. Field of the Invention

The present invention relates to a process for purifying allyl alcohol. More particularly, the present invention relates to a process for obtaining allyl alcohol having a high purity by efficiently removing water from an aqueous solution of allyl alcohol.

2. Description of the Related Art

Allyl alcohol is an industrially valuable substance used for the synthesis of various chemicals such as glycerol and diallyl phthalate and as an intermediate for the synthesis of synthetic resins.

As the process for preparing allyl alcohol, there is known a process in which, as indicated by the following reaction formulae (1) and (2), allyl chloride is formed by high-temperature chlorination of propylene and allyl chloride is subjected to alkali hydrolysis:

(1)

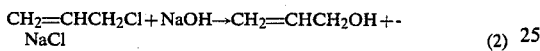
(2)

This process is defective in that expensive chlorine should be used in a large amount and since hydrogen chloride gas is handled, corrosion of apparatus is serious.

Another process is known in which allyl alcohol is prepared by isomerization of propylene oxide using lithium phosphate as a catalyst:

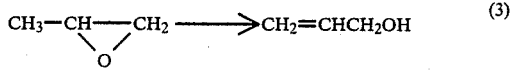
(3)

This process is also defective in that the starting material is expensive.

Recently, there has been proposed a process in which propylene is used as the starting material and allyl alcohol is prepared without handling chlorine or hydrogen chloride. According to this process, as indicated by the following formulae (3) and (4), propylene is reacted in the presence of acetic acid with oxygen or an oxygen-containing gas by using a catalyst comprising an alkaliacetate and palladium, optionally together with a copper compound, supported on a carrier, in the gas phase, at 100° to 300° C. and 0 to 30 atmospheres (gauge pressure), to obtain allyl acetate, formed allyl acetate is collected by cooling, an aqueous solution of acetic acid is added to collected allyl acetate to form a homogeneous solution, the homogeneous solution is passed through a tubular reaction vessel filled with a strong-acid cation-exchange resin and heated by a heating medium, and the reaction liquid is subjected to distillation to obtain allyl alcohol [see, Japanese Unexamined Patent Publication (Kokai) No. 60-32747 and Japanese Unexamined Patent Publication (Kokai) No. 60-258171]:

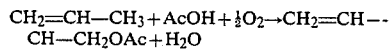
(4)

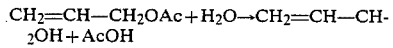
(5)

According to this preparation process, allyl alcohol is obtained in the form of an aqueous solution. However, since allyl alcohol (having a boiling point of 96° to 97° C.) forms an azeotropic mixture (having a boiling point of 87.5° C.) with water, water cannot be removed only by distillation.

SUMMARY OF THE INVENTION

It is an object of the present invention to provide a purification process in which allyl alcohol having a high purity is obtained by removing water from allyl alcohol prepared in the form of an aqueous solution.

Thus, in order to attain the above-mentioned object, the present invention provides a process for purifying allyl alcohol, which comprises adding at least one potassium salt selected from the group consisting of dipotassium hydrogenphosphate, potassium phosphate, potassium pyrophosphate, potassium tripolyphosphate and potassium carbonate to an aqueous solution of allyl alcohol to separate the solution into an aqueous phase and an organic phase, removing the aqueous phase, and subjecting the organic phase to distillation to obtain allyl alcohol having a high purity.

BRIEF DESCRIPTION OF THE DRAWING

The FIGURE is a flow chart of an example of an industrial process utilizing the purification process of the present invention.

DESCRIPTION OF THE PREFERRED EMBODIMENTS

As means for removing water from an aqueous solution of allyl alcohol, there may be considered a process in which, as practised for ethanol or isopropanol, a large amount of a third component such as benzene is added as an entrainer and separation is effected by distillation. However, in case of allyl alcohol, this process is not practical because the water content in the azeotropic mixture is high and a great quantity of energy is necessary for the separation.

It has hitherto been known that when a salt is added to a homogeneous mixture of an organic substance and water, the mixture is separated into two phases, and this phenomenon is often utilized for the liquid-separating operation. We made research with a view to obtaining allyl alcohol having a high purity by efficiently removing water from an aqueous solution of allyl alcohol having a composition close to the azeotropic composition by utilizing this phenomenon.

When a salt customarily used, such as sodium chloride (NaCl), is added in a saturation amount to an aqueous solution of allyl alcohol, the water content is merely reduced to about 20% from the initial level of about 30%, and it is confirmed that the process is industrially insufficient. It have been found that dipotassium hydrogenephosphate ($K_2HPO_4$), potassium phosphate ($K_3PO_4$), potassium pyrophosphate ($K_4P_2O_7$), potassium tripolyphosphate ($K_5P_3O_{10}$) and potassium carbonate ($K_2CO_3$) are very effective for attaining the above-mentioned object. We have now completed the present invention based on this finding.

According to the purification process of the present invention, dipotassium hydrogenphospate, potassium phosphate, potassium pyrophosphate, potassium tripolyphosphate and/or potassium carbonate (these salts may be anhydrous salts or may contain water of crystallization) is added in the form of a solid or a concentrated aqueous solution to an aqueous solution of allyl alcohol, and the mixture is stirred to dissolve the added salt and the solution is allowed to stand still to separate it into an organic phase and an aqueous phase.

As the amount added of the salt is larger, the water content is proportionally reduced in the separated organic phase (allyl alcohol phase) and better results are obtained. However, if the salt is added in an amount exceeding the saturation amount, troubles are caused by precipitation of the salt, and the process becomes disadvantageous from the industrial viewpoint.

Water solubilities of dipotassium hydrogenphosphate, potassium phosphate, potassium pyrophosphate, and potassium carbonate are as shown in Table 1 given below [Handbook of Chemistry, 3rd edition, Basic Volume II, page 170 (compiled by the Japanese Chemical Association)]. Potassium tripolyphosphate has a water solubility of about 67% at 20° C. [Ullmanns Encyklopädie der Technichen Chimie, Volume 18, page 332]. It is necessary that care should be taken so that the salt concentration does not exceed the saturation concentration at the operation temperature.

TABLE I

| Temperature (°C.) | Water Solubilities (% by weight) | | | |
| --- | --- | --- | --- | --- |
|  | $K_2HPO_4.xH_2O$* | $K_2CO_3.3/2H_2O$ | $K_3PO_4.nH_2O$* | $K_4P_2O_7.7/2H_2O$ |
| 25 | 62.0 | 52.85 | 51.42 | — |
| 30 | 63.2 | 53.2 | 53.08 | 66.7 |
| 40 | 66.6 | 53.9 | 62.73 | — |
| 50 | 71.9 | 54.8 | 63.6–63.8 | 67.33 |
| 60 | 72.2 | 55.9 | 64.08 | — |
| 70 | — | — | — | 68.81 |
| 80 | 72.2 | 58.3 | — | — |

Note
When the temperature is 25 to 40° C., x is 3 and n is 7, and when the temperature is 50° C. or higher, x is 0 and n is 3.

When a mixture of dipotassium phosphate and a cheaper salt (such as sodium carbonate) is used, a high effect can be attained by using a small amount of dipotassium phosphate.

According to the purification process of the present invention, the water content can be reduced to 5 to 10% in an aqueous solution of allyl alcohol having a composition (water content of about 30%) close to the azeotropic composition, and if the remaining organic phase is subjected to distillation, allyl alcohol having a high purity can be obtained as the main distillate. By ordinary distillation, allyl alcohol having a purity of 98 to 99% or more can be easily obtained. Furthermore, the azeotropic mixture obtained as the initial distillate can be utilized as the starting material of the purification process again. Furthermore, if water is evaporated from the aqueous phase, the salt can be recovered in the form of a concentrated solution or a solid, and this salt can be recycled and used again.

A flow chart of an example of an industrial process utilizing the purification process of the present invention is shown in the FIGURE.

In this example, the starting aqueous solution 1 of allyl alcohol (allyl alcohol/water ratio=about 70/30) and at least one of the above-mentioned salts 2 are sufficiently stirred in a mixing tank B to dissolve the salt, and the solution is allowed to stand still in a phase separator C to separate the solution into an aqueous phase 4 and an organic phase 5. In a distillation column D, the azeotropic mixture is removed from the organic phase (allyl alcohol phase) 5 and the azeotroic mixture is returned to the mixing tank B. The water-free bottom residue is subjected to distillation in a distillation column E. Allyl alcohol 8 containing a small amount of the salt is returned to the phase separator through a line 3. The majority of water is evaporated from the aqueous phase containing a large amount of the salt in a water evaporator A and the residue is recycled to the mixing tank.

In the process for purifying allyl alcohol according to the present invention, the water content is reduced to 5 to 10% in the allyl alcohol phase obtained by the phase separation. Accordingly, the quantity of steam necessary for the subsequent distillation refining is much smaller than in the conventional distillation process.

The salt used for the phase separation has not a corrosive action as possessed by a chloride or the like. Accordingly, an apparatus composed of a cheap material can be used.

The purification process of the present invention will now be described with reference to the following examples and comparative examples. Incidentally, all of "%" in the following description are by weight.

EXAMPLE 1

To 300 ml of a solution comprising 30.8% of water and 69.2% of allyl alcohol was added 160 g of dipotassium hydrogenphosphate (anhydride), and the mixture was shaken at 40° C. for 10 minutes and was then allowed to stand still, whereby the liquid was separated into two phases. The volume ratio of the organic phase to the aqueous phase was about 1.8. The upper organic phase was composed mainly of allyl alcohol, and from the results of the analysis by the Karl Fischer's method, it was found that the water content was reduced to 5.0%. From the results of the analysis by the neutralization titration, it was found that dipotassium phosphate was contained only in an amount of 0.01%.

The lower aqueous phase consisted of a concentrated aqueous solution of the salt, and from the results of the analysis by the gas chromatography, it was found that the allyl alcohol content was as low as 0.013%.

EXAMPLE 2

The treatment was carried out in the same manner as described in Example 1 except that the amount added of dipotassium hydrogenphosphate was changed to 80 g and the operation was carried out at room temperature. It was found that the water content in the upper phase was reduced to 9.7% and the salt content was as low as 0.02%. Furthermore, the allyl alcohol content in the lower phase was only 0.02%

EXAMPLE 3

To 300 ml of a solution comprising 70.1% of allyl alcohol and 29.9% of water was added 90 g of potassium carbonate (anhydride), and the mixture was shaken at room temperature for 10 minutes. A part of the salt was left undissolved, but when the mixture was allowed to stand still, the liquid phase was separated into two phases.

When the allyl alcohol phase was analyzed, it was found that the water content was reduced to 5.4% and the salt content was 2.6%. In the aqueous phase, the allyl alcohol content was as low as 0.13%.

EXAMPLE 4

To 300 ml of a solution comprising 71.5% of allyl alcohol and 28.5% of water was added 300 ml of a saturated aqueous solution of dipotassium hydrogenphosphate, and the mixture was stirred and allowed to stand still, whereby the mixture was separated into two phases. It was found that the water content in the allyl alcohol phase was reduced to 9.8%. Water in the aqueous phase was evaporated and the aqueous phase was concentrated almost to the saturation concentration. This operation was repeated 10 times. In each case, the water content in the allyl alcohol phase was 9.7 to 9.8%, and the obtained results had a good reproducibility.

When the obtained allyl alcohol phase was subjected to distillation in an Oldershaw column type distillation apparatus, a mixture comprising 72% of allyl alcohol and 28% of water and having a composition close to the azeotropic composition was obtained from the column head, while allyl alcohol substantially free of water, having a water content of 0.2%, was obtained from the column bottom.

EXAMPLE 5

The procedures of Example 1 were repeated in the same manner except that the amount used of dipotassium hydrogenphosphate was changed to 80 g and sodium carbonate was further added in a saturation amount. It was found that the water content in the allyl alcohol phase was reduced to 6.0% and the salt content was lower than 0.1%. In the lower phase (aqueous phase), the allyl alcohol content was low as 0.01%.

COMPARATIVE EXAMPLE 1

The procedures of Example 3 were repeated in the same manner except that sodium chloride was used in an amount much larger than the saturation amount instead of potassium carbonate. The water content in the allyl alcohol phase was 20%.

COMPARATIVE EXAMPLE 2

The procedures of Comparative Example 1 were repeated in the same manner except that disodium hydrogenphosphate was used instead of sodium chloride. The liquid was not separated into two phases.

COMPARATIVE EXAMPLE 3

The procedures of Comparative Example 1 were repeated in the same manner except that sodium dihydrogenphosphate was used instead of sodium chloride. In the allyl alcohol phase, the water content was 19.8% and the salt content was 0.4%. In the aqueous phase, the allyl alcohol content was 0.9%.

COMPARATIVE EXAMPLE 4

The procedures of Comparative Example 1 were repeated in the same manner except that sodium carbonate was used instead of sodium chloride. The volume of the aqueous phase was about ½ of the volume of the aqueous phase in Comparative Example 1, and separation of water from allyl alcohol was insufficient.

EXAMPLE 6

To 500 ml of a solution (A) comprising 30% of water and 70% of allyl alcohol was added a solution (B) of 320 g of potassium phosphate in 180 g of water, and the mixture was vigorously agitated and was then allowed to stand still, whereby the liquid was separated into two phases. The upper phase was composed mainly of allyl alcohol, and it was found that the water content 11.5% and the potassium phosphate content was 0.87%.

The lower phase consisted mainly of a concentrated aqueous solution of potassium phosphate, and it was found that the allyl alcohol content was 0.72%.

When the upper allyl alcohol phase was subjected to distillation in an Oldershaw column type distillation apparatus, a mixture comprising 74% of allyl alcohol and 26% of water having a composition close to the azeotropic composition was obtained from the column head, while allyl alcohol substantially free of water, having a water content of 0.15%, was obtained from the column bottom. The liquid obtained from the column bottom was colored yellow. When the yellow liquid was subjected to distillation until 95% of the liquid was distilled off, the distillate was pure allyl alcohol and the colored material and potassium phosphate were retained at the bottom of the distillation still.

EXAMPLE 7

50 ml of a solution comprising 66.2% of allyl alcohol and 33.8% of water was introduced into a separatory funnel, potassium phosphate was added in portions while shaking the mixture until potassium phosphate no more dissolved therein. The mixture was then allowed to stand still, whereby the liquid was separated into two phases. The upper phase was composed mainly of allyl alcohol and the water content was reduced to 4.8%.

EXAMPLE 8

The treatment was carried out in the same manner as described in Example 7 except that potassium pyrophosphate was used instead of potassium phosphate. It was found that the water content in the upper phase was reduced to 6.7%

EXAMPLES 9 THROUGH 11

The treatment was carried out in the same manner as described in Example 6 except that 60% aqueous solution of potassium pyrophosphate was used as the solution (B) and the added amount thereof was changed to 250 g, 500 g or 1,000 g. The results were as shown in Table 2.

TABLE 2

| Example No. | Amount of potassium pyrophosphate solution (g) | Water content in upper phase (%) | Residue of upper phase distillation* (%) |
|---|---|---|---|
| 9 | 250 | 19.8 | 0.11 |
| 10 | 500 | 14.0 | 0.070 |
| 11 | 1,000 | 11.9 | 0.058 |

Note
*The residue was composed mainly of potassium pyrophosphate.

EXAMPLE 12

The procedures of Example 7 were repeated in the same manner except that potassium tripolyphosphate was used instead of potassium phosphate. The water content in the upper phase was 6.5%.

COMPARATIVE EXAMPLE 5

The procedures of Comparative Example 1 were repeated in the same manner except that sodium phosphate was used instead of sodium chloride. The liquid was not separated into two phases.

I claim:

1. A process for purifying allyl alcohol, consisting essentially of adding at least one potassium salt selected from the group consisting of dipotassium hydrogenphosphate, potassium phosphate, potassium pyrophosphate, and potassium tripolyphosphate to an aqueous solution of allyl alcohol to separate the solution into an aqueous phase and an organic phase, and removing the aqueous phase.

2. A process as set forth in claim 1, wherein the organic phase is then subjected to distillation to obtain allyl alcohol having a high purity.

3. A process as set forth in claim 1, wherein said potassium salt is in the form of an anhydrous salt.

4. A process as set forth in claim 1, wherein said potassium salt is in the form of a hydrated salt.

* * * * *